United States Patent
Sunkavalli et al.

(10) Patent No.: US 10,181,199 B2
(45) Date of Patent: Jan. 15, 2019

(54) MATERIAL CAPTURE USING IMAGING

(71) Applicant: ADOBE SYSTEMS INCORPORATED, San Jose, CA (US)

(72) Inventors: Kalyan Krishna Sunkavalli, San Jose, CA (US); Sunil Hadap, Dublin, CA (US); Joon-Young Lee, Milpitas, CA (US); Zhuo Hui, Pittsburgh, PA (US)

(73) Assignee: ADOBE SYSTEMS INCORPORATED, San Jose, CA (US)

( * ) Notice: Subject to any disclaimer, the term of this patent is extended or adjusted under 35 U.S.C. 154(b) by 60 days.

(21) Appl. No.: 15/589,757

(22) Filed: May 8, 2017

(65) Prior Publication Data
US 2018/0322644 A1 Nov. 8, 2018

(51) Int. Cl.
*G06T 3/00* (2006.01)
*G06T 7/49* (2017.01)
*G06T 7/60* (2017.01)
*G06T 17/00* (2006.01)

(52) U.S. Cl.
CPC .............. *G06T 7/49* (2017.01); *G06T 3/0068* (2013.01); *G06T 7/60* (2013.01); *G06T 17/00* (2013.01); *G06T 2200/08* (2013.01)

(58) Field of Classification Search
CPC G06T 7/49; G06T 7/60; G06T 3/0068; G06T 17/00; G06T 2200/08
See application file for complete search history.

(56) References Cited

U.S. PATENT DOCUMENTS

| | | | | |
|---|---|---|---|---|
| 9,367,909 | B2* | 6/2016 | Tin | G06T 7/0004 |
| 2004/0150643 | A1* | 8/2004 | Borshukov | G06T 13/80 |
| | | | | 345/426 |
| 2015/0256810 | A1* | 9/2015 | Chandaker | G01B 11/24 |
| | | | | 348/50 |
| 2018/0047208 | A1* | 2/2018 | Marin | G06T 11/001 |
| 2018/0241908 | A1* | 8/2018 | Kishimoto | H04N 1/4072 |

OTHER PUBLICATIONS

Aittala, M., Aila, T., & Lehtinen, J. (2016). Reflectance modeling by neural texture synthesis. ACM Transactions on Graphics (TOG), 35(4), 65.
Aittala, M., Weyrich, T., & Lehtinen, J. (2015). Two-shot SVBRDF capture for stationary materials. ACM Trans. Graph., 34(4), 110-1.
Alldrin, N., Zickler, T., & Kriegman, D. (2008). Photometric stereo with non-parametric and spatially-varying reflectance.
(Continued)

*Primary Examiner* — Brenda C Bernardi
(74) *Attorney, Agent, or Firm* — Shook, Hardy & Bacon, L.L.P.

(57) ABSTRACT

Methods and systems are provided for performing material capture to determine properties of an imaged surface. A plurality of images can be received depicting a material surface. The plurality of images can be calibrated to align corresponding pixels of the images and determine reflectance information for at least a portion of the aligned pixels. After calibration, a set of reference materials from a material library can be selected using the calibrated images. The set of reference materials can be used to determine a material model that accurately represents properties of the material surface.

20 Claims, 7 Drawing Sheets

(56) References Cited

OTHER PUBLICATIONS

Barron, J. T., & Malik, J. (Oct. 2012). Color constancy, intrinsic images, and shape estimation. In European Conference on Computer Vision (pp. 57-70). Springer, Berlin, Heidelberg.

Barron, J. T., & Malik, J. (2015). Shape, illumination, and reflectance from shading. IEEE transactions on pattern analysis and machine intelligence, 37(8), 1670-1687.

Debevec, P., Hawkins, T., Tchou, C., Duiker, H. P., Sarokin, W., & Sagar, M. (Jul. 2000). Acquiring the reflectance field of a human face. In Proceedings of the 27th annual conference on Computer graphics and interactive techniques (pp. 145-156). ACM Press/Addison-Wesley Publishing Co.

Einarsson, P., Chabert, C. F., Jones, A., Ma, W. C., Lamond, B., Hawkins, T., . . . & Debevec, P. E. (2006). Relighting Human Locomotion with Flowed Reflectance Fields. Rendering techniques, 2006, 17th.

Goldman, D. B., Curless, B., Hertzmann, A., & Seitz, S. M. (2010). Shape and spatially-varying BRDFs from photometric stereo. IEEE Transactions on Pattern Analysis and Machine Intelligence, 32(6), 1060-1071.

Hui, Z., & Sankaranarayanan, A. C. (Apr. 2015). A dictionary-based approach for estimating shape and spatially-varying reflectance. In Computational Photography (ICCP), 2015 IEEE International Conference on (pp. 1-9). IEEE.

Jakob, W., & Marschner, S. (2012). Manifold exploration: a Markov Chain Monte Carlo technique for rendering scenes with difficult specular transport. ACM Transactions on Graphics (TOG), 31(4), 58.

Matusik, W. (2003). A data-driven reflectance model (Doctoral dissertation, Massachusetts Institute of Technology).

Riviere, J., Peers, P., & Ghosh, A. (Feb. 2016). Mobile surface reflectometry. In Computer Graphics Forum (vol. 35, No. 1, pp. 191-202).

Romeiro, F., Vasilyev, Y., & Zickler, T. (Oct. 2008). Passive reflectometry. In European Conference on Computer Vision (pp. 859-872). Springer, Berlin, Heidelberg.

Romeiro, F., & Zickler, T. (Sep. 2010). Blind reflectometry. In European conference on computer vision (pp. 15-58). Springer, Berlin, Heidelberg.

Rusinkiewicz, S. M. (1998). A new change of variables for efficient BRDF representation. In Rendering techniques' 98 (pp. 11-22). Springer, Vienna.

Zhao, S., Jakob, W., Marschner, S., & Bala, K (2012). Structure-aware synthesis for predictive woven fabric appearance. ACM Transactions on Graphics (TOG), 31(4), 75.

\* cited by examiner

MATERIAL CAPTURE USING IMAGING

BACKGROUND

Oftentimes, users desire to use the appearance of real-world objects as references for the surfaces of computer-generated objects; for example, using the appearance of a wood-grain desk in their workspace as a reference for the surface of a computer-generated desk. Creating a model of surface properties can allow the appearance of real-world objects to be applied in such a manner. Determining a bi-directional reflectance distribution function (BRDF) that defines how light is reflected at a surface can be used to create such a material model. Finding a BRDF of a surface allows for capture of the appearance of real-world surfaces for use as references when rendering computer-generated objects to produce high-quality photorealistic content. As such, the process of determining a material model that can accurately assign the appearance of material surface to a computer-generated object can be known as BRDF capture.

Currently, BRDF capture can be performed using imaging to determine information about the appearance of a surface of a real-world object. Typically, to perform BRDF capture, existing techniques rely on complex setups to collect photographs under a multitude of staged lighting conditions. The requirements of such a set-up make BRDF capture impracticable and inefficient as use of these complex systems is highly costly and requires significant time and effort. Approaches that attempt to overcome such complex system setups are limited to BRDF capture of highly uniform material surfaces where there are little to no variations in the surface properties across the material surface. As such, these approaches fail to allow for accurate BRDF capture of surfaces with material variations, for example, differences in wood grain texture, etchings in a metal surface, or variations in leather coloration across a captured surface.

SUMMARY

Embodiments of the present invention are directed towards enabling accurate material capture of the properties of a surface. In accordance with embodiments of the present invention, material capture uses imaging to create a model of material properties of a surface that can be used to assign the properties to the surface of a computer-generated object. To generate an accurate material model, material capture takes images of a surface in a real-world setting. Once gathered, this information can be used to build a material model that estimates the reflectance properties of the material surface to accurately reproduce the visual appearance of the material surface using computer graphics.

Creating such a material model can be accomplished by capturing images of a real-world surface. These images can then be calibrated by aligning the pixels of the images to compile the different lighting/camera position information available from each captured image at each pixel. This lighting/camera position information can be used to select a set of reference materials that can be used to extrapolate the material properties of the imaged material surface. Such a library of referenced materials can be narrowed to a set that represents the properties of the imaged material surface. This subset of reference materials can then be used to estimate the properties of the imaged material surface based on previously determined material properties of the reference materials. Specifically, the properties of the imaged material surface can be determined by iteratively using the previously determined material properties of the reference materials until a material model is produced that is representative of the properties of the imaged material surface. Such a material model can then be used to reproduce the visual appearance of the imaged material surface for surfaces of computer-generated objects.

DETAILED DESCRIPTION

Figure 1:
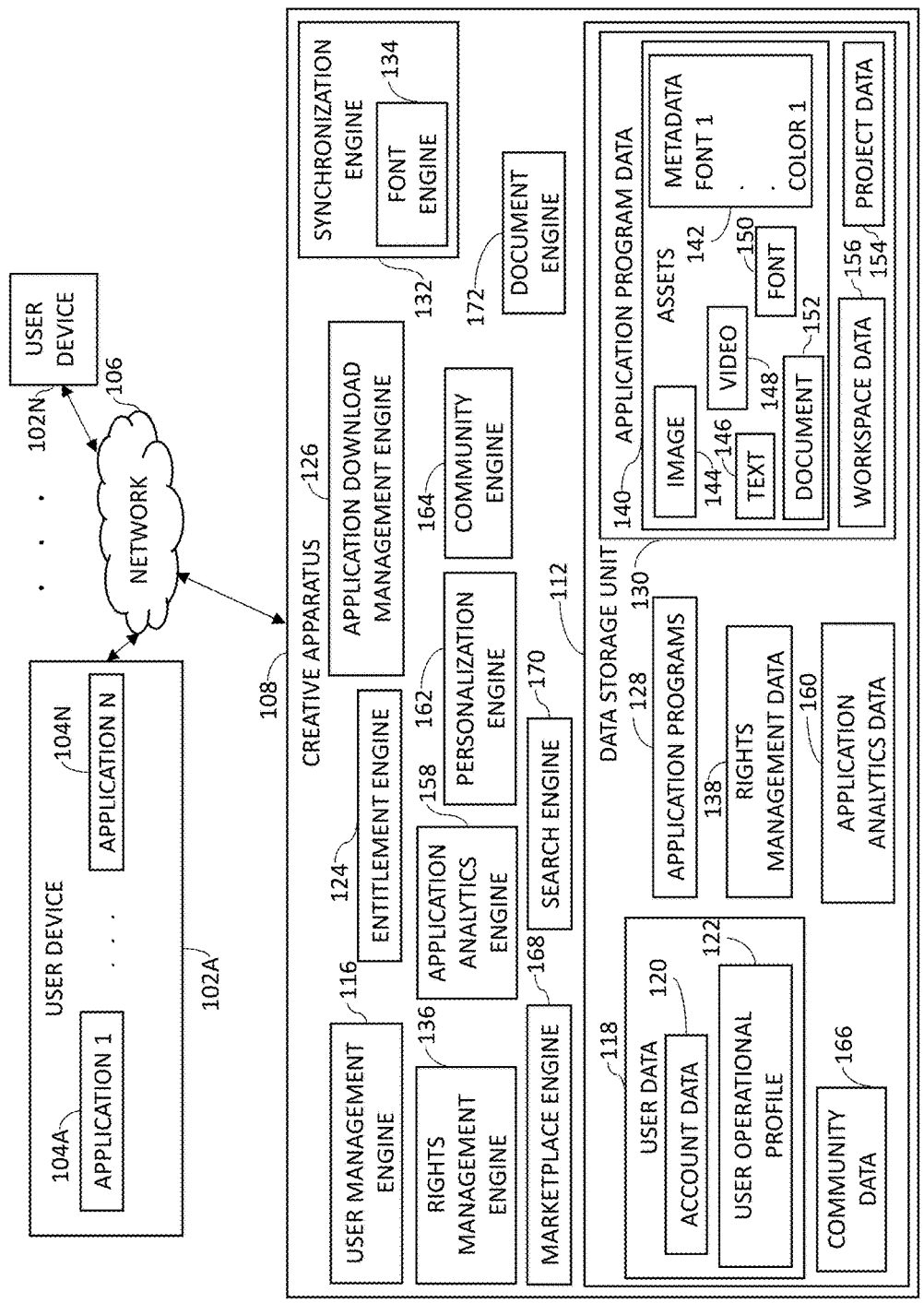
FIG. 1 depicts a diagram of an environment in which one or more embodiments of the present disclosure can be practiced, in accordance with various embodiments of the present disclosure.

When rendering computer-generated objects, users oftentimes want to utilize the appearance of real-world objects to guide the appearance assigned to the surfaces of objects during rendering. For example, a user may wish to create a computer-generated image of a desk that imitates the appearance of a wood-grain desk in their workspace. Accurate determination of the properties of the material(s) that comprise the surface of a real-world object enables the creation of a material model of the surface material of the object. Such a material model can then be applied when creating computer-generated objects. Creating material models can be performed using a bi-directional reflectance distribution function (BRDF). A BRDF is a function that defines how light is reflected at a surface. The function takes incoming light direction and outgoing light direction to determine the ratio of reflected radiance to the irradiance incident on the surface. Determining a BRDF can aid in capturing of the appearance of real-world surfaces as a material model to use as a reference when rendering a computer-generated object to produce high-quality photorealistic content. As such, the process of determining a material model that can accurately assign the appearance of material surface to a computer-generated object can be known as material capture.

Generally, in material capture, the reflectance of a material(s), which can be represented as a BRDF, that comprises a surface of an object is sampled using a variety of lighting-view combinations. Once gathered, this reflectance information can be used to build a material model that estimates the properties of the surface to accurately reproduce the appearance of the surface using computer graphics. As such, a material model determined using material capture can be used in computer graphics to assign information taken from a real-world surface, such as color, patterning, and/or lighting, to a surface of an computer-generated object during rendering.

Existing methods to determine a BRDF of a material surface utilize complex acquisition systems to collect surface material information. Such complex systems make material capture impracticable and inefficient, as use of these systems is costly in time, money, and effort. While approaches have been introduced that attempt to overcome such limitations by minimizing the complexity of the setup, such approaches are limited to determining a BRDF for stationary textures. Stationary textures belong to material surfaces with a large degree of redundancy in that there are multiple points on the material surface that exhibit identical, or highly similar, surface properties. As such, these approaches use this similarity to combine information from multiple places on the surface to determine surface properties of the material surface as a whole. However, using this approach and relying on similarities across a surface result in the assumption that the surface has the same properties at points (e.g., all points) across a sample. Such an assumption prevents accurate capture of surfaces which have distinct textures in different regions.

For example, one conventional method employs the use of two images, one taken with a flash and one taken without a flash, where the flash image provides lighting-dependent samples of the material surface and the non-flash image allows for identification of similar areas across the surface. These images can then be used to determine various areas across the flash image for which to gather the information necessary to determine the BRDF for the surface. As such, reflectance information is augmented using multiple areas of a surface to synthesize reflectance samples of the surface. Because only one measurement of reflectance information per pixel exists, such a method is not capable of determining a BRDF at each pixel on the surface without using the augmented information. However, when such augmented information is used, the determined BRDF no longer accurately captures variations in the surface and instead finds an average BRDF across the surface as a whole. As such, this method only works for stationary textures and cannot handle surfaces with distinct patterns or other such surface variations. Thus, such approaches fail to allow for accurate determination of a model indicating variations in BRDF across surfaces due to surface and/or material property variations, such as, for example, differences in wood grain texture, differences in etchings in a metal surface, or variations in leather coloration.

As such, embodiments of the present invention are directed towards facilitating efficient and effective modeling of material properties, such as reflectance, of a surface using material capture. Specifically, material capture uses a simplistic setup while still allowing accurate capture of non-stationary textures, such as, determining accurate material models for material surfaces with irregularities, dissimilarities, or other such variations across the surfaces. Such an accurate material model is possible because multiple measurements of reflectance information are collected at individual pixels across the surface which can be used to determine variations in BRDF across surface. In this way, embodiments of the present invention can allow for determining a per-pixel BRDF of a material surface.

At a high level, in accordance with embodiments of the present invention, to perform such material capture, multiple images of a material surface can be taken and aligned without user intervention to determine lighting/view directions, compiled from images at corresponding pixels. In this way, images can be taken of a real-world surface using any device with image capturing capabilities, such as, for example, a mobile phone. These images can then be calibrated by aligning the images and determining the different lighting/camera position information available from each image at corresponding pixels across the imaged surface. Such calibrated images can be used to determine the BRDF and shape of the object surface, where the shape can be characterized by surface normals. A surface normal is a vector that is perpendicular to the tangent plane at a point, or pixel, on the surface.

When determining material properties of a surface during material capture, reflectance information about a surface material can be estimated using a database, such as a material library, of reference materials that have had such information previously calculated. As such, the BRDF at a pixel can be represented using a subset of reference materials selected from a dictionary of reference materials. The BRDF at a pixel can be expressed using the various reference materials used to determine an accurate material model for the properties of the surface material. Advantageously, using a compilation of such reference materials to represent the properties of the surface material greatly reduces the number of unknowns that must be determined to find the BRDF. Specifically, instead of having to solving for a high-dimensional vector, only percentages of contribution from the reference materials needs to be solved for each pixel.

To determine the BRDF at a pixel using such reference materials, iterative updates can be performed until the error in the output is reduced to below a predetermined threshold. To perform this determination, given the reference materials, and the coefficient of abundance based on the subset of reference materials, the surface normal can be solved for by searching for estimates of the surface normals that minimize the energy function. Upon finding new surface normals, the new surface normals can then be used to solve for new abundances. This process can be iteratively performed until the output falls below a predetermined threshold level.

Turning to FIG. 1, FIG. 1 is a diagram of an environment 100 in which one or more embodiments of the present disclosure can be practiced. The environment 100 includes one or more user devices, such as user devices 102A-102N. Examples of a user device include, but are not limited to, a personal computer (PC), a tablet computer, a desktop computer, a processing unit, any combination of these devices, or any other suitable device having one or more processors. Each user device can include at least one application supported by the creative apparatus 108. It is to be appreciated that following description may generally refer to the user device 102A as an example and any other user device can be used.

A user of the user device can utilize various products, applications, or services supported by the creative apparatus 108 via the network 106. The user devices 102A-102N can be operated by various users. Examples of the users include, but are not limited to, creative professionals or hobbyists who use creative tools to generate, edit, track, or manage creative content, advertisers, publishers, developers, content owners, content managers, content creators, content viewers, content consumers, designers, editors, any combination of these users, or any other user who uses digital tools to create, edit, track, or manages digital experiences.

A digital tool, as described herein, includes a tool that is used for performing a function or a workflow electronically. Examples of a digital tool include, but are not limited to, content creation tool, content editing tool, content publishing tool, content tracking tool, content managing tool, content printing tool, content consumption tool, any combination of these tools, or any other tool that can be used for creating, editing, managing, generating, tracking, consuming or performing any other function or workflow related to content. A digital tool includes the creative apparatus 108.

Digital experience, as described herein, includes experience that can be consumed through an electronic device. Examples of the digital experience include content creating, content editing, content tracking, content publishing, content posting, content printing, content managing, content viewing, content consuming, any combination of these experiences, or any other workflow or function that can be performed related to content.

Content, as described herein, includes electronic content. Examples of the content include, but are not limited to, image, video, website, webpage, user interface, menu item, tool menu, magazine, slideshow, animation, social post, comment, blog, data feed, audio, advertisement, vector graphic, bitmap, document, any combination of one or more content, or any other electronic content.

User devices 102A-102N can be connected to a creative apparatus 108 via a network 106. Examples of the network 106 include, but are not limited to, internet, local area network (LAN), wireless area network, wired area network, wide area network, and the like.

The creative apparatus 108 includes one or more engines for providing one or more digital experiences to the user. The creative apparatus 108 can be implemented using one or more servers, one or more platforms with corresponding application programming interfaces, cloud infrastructure and the like. In addition, each engine can also be implemented using one or more servers, one or more platforms with corresponding application programming interfaces, cloud infrastructure and the like. The creative apparatus 108 also includes a data storage unit 112. The data storage unit 112 can be implemented as one or more databases or one or more data servers. The data storage unit 112 includes data that is used by the engines of the creative apparatus 108.

A user of the user device 102A visits a webpage or an application store to explore applications supported by the creative apparatus 108. The creative apparatus 108 provides the applications as a software as a service (SaaS), or as a standalone application that can be installed on the user device 102A, or as a combination. The user can create an account with the creative apparatus 108 by providing user details and also by creating login details. Alternatively, the creative apparatus 108 can automatically create login details for the user in response to receipt of the user details. In some embodiments, the user is also prompted to install an application manager. The application manager enables the user to manage installation of various applications supported by the creative apparatus 108 and also to manage other functionalities, such as updates, subscription account and the like, associated with the applications. The user details are received by a user management engine 116 and stored as user data 118 in the data storage unit 112. In some embodiments, the user data 118 further includes account data 120 under which the user details are stored.

The user can either opt for a trial account or can make payment based on type of account or subscription chosen by the user. Alternatively, the payment can be based on product or number of products chosen by the user. Based on payment details of the user, a user operational profile 122 is generated by an entitlement engine 124. The user operational profile 122 is stored in the data storage unit 112 and indicates entitlement of the user to various products or services. The user operational profile 122 also indicates type of user, i.e. free, trial, student, discounted, or paid.

In some embodiment, the user management engine 116 and the entitlement engine 124 can be one single engine performing the functionalities of both the engines.

The user can then install various applications supported by the creative apparatus 108 via an application download management engine 126. Application installers or application programs 128 present in the data storage unit 112 are fetched by the application download management engine 126 and made available to the user directly or via the application manager. In one embodiment, an indication of all application programs 128 are fetched and provided to the user via an interface of the application manager. In another embodiment, an indication of application programs 128 for which the user is eligible based on user's operational profile are displayed to the user. The user then selects the application programs 128 or the applications that the user wants to download. The application programs 128 are then downloaded on the user device 102A by the application manager via the application download management engine 126. Corresponding data regarding the download is also updated in the user operational profile 122. An application program 128 is an example of the digital tool. The application download management engine 126 also manages the process of providing updates to the user device 102A.

Upon download, installation and launching of an application program, in one embodiment, the user is asked to provide the login details. A check is again made by the user management engine 116 and the entitlement engine 124 to ensure that the user is entitled to use the application program. In another embodiment, direct access is provided to the application program as the user is already logged into the application manager.

The user uses one or more application programs 104A-104N installed on the user device to create one or more projects or assets. In addition, the user also has a workspace within each application program. The workspace, as described herein, includes setting of the application program, setting of tools or setting of user interface provided by the application program, and any other setting or properties specific to the application program. Each user can have a workspace. The workspace, the projects, and/or the assets can be stored as application program data 130 in the data storage unit 112 by a synchronization engine 132. Alternatively or additionally, such data can be stored at the user device, such as user device 102A.

The application program data 130 includes one or more assets 140. The assets 140 can be a shared asset which the user wants to share with other users or which the user wants to offer on a marketplace. The assets 140 can also be shared across multiple application programs 128. Each asset includes metadata 142. Examples of the metadata 142 include, but are not limited to, font, color, size, shape, coordinate, a combination of any of these, and the like. In addition, in one embodiment, each asset also includes a file. Examples of the file include, but are not limited to, an image 144, text 146, a video 148, a font 150, a document 152, a combination of any of these, and the like. In another embodiment, an asset only includes the metadata 142.

The application program data 130 also include project data 154 and workspace data 156. In one embodiment, the project data 154 includes the assets 140. In another embodiment, the assets 140 are standalone assets. Similarly, the workspace data 156 can be part of the project data 154 in one embodiment while it may be standalone data in other embodiment.

A user can operate one or more user devices to access data. In this regard, the application program data 130 is accessible by a user from any device, including a device which was not used to create the assets 140. This is achieved by the synchronization engine 132 that stores the application program data 130 in the data storage unit 112 and enables the application program data 130 to be available for access by the user or other users via any device. Before accessing the application program data 130 by the user from any other device or by any other user, the user or the other user may need to provide login details for authentication if not already logged in. In some cases, if the user or the other user are logged in, then a newly created asset or updates to the application program data 130 are provided in real time. The rights management engine 136 is also called to determine whether the newly created asset or the updates can be provided to the other user or not. The workspace data 156 enables the synchronization engine 132 to provide a same workspace configuration to the user on any other device or to the other user based on the rights management data 138.

In various embodiments, various types of synchronization can be achieved. For example, the user can pick a font or a color from the user device 102A using a first application program and can use the font or the color in a second application program on any other device. If the user shares the font or the color with other users, then the other users can also use the font or the color. Such synchronization generally happens in real time. Similarly, synchronization of any type of the application program data 130 can be performed.

In some embodiments, user interaction with the applications 104 is tracked by an application analytics engine 158 and stored as application analytics data 160. The application analytics data 160 includes, for example, usage of a tool, usage of a feature, usage of a workflow, usage of the assets 140, and the like. The application analytics data 160 can include the usage data on a per user basis and can also include the usage data on a per tool basis or per feature basis or per workflow basis or any other basis. The application analytics engine 158 embeds a piece of code in the applications 104 that enables the application to collect the usage data and send it to the application analytics engine 158. The application analytics engine 158 stores the usage data as the application analytics data 160 and processes the application analytics data 160 to draw meaningful output. For example, the application analytics engine 158 can draw an output that the user uses "Tool 4" maximum number of times. The output of the application analytics engine 158 is used by a personalization engine 162 to personalize tool menu for the user to show "Tool 4" on top. Other types of personalization can also be performed based on the application analytics data 158. In addition, the personalization engine 162 can also use the workspace data 156 or the user data 118 including user preferences to personalize one or more application programs 128 for the user.

In some embodiments, the application analytics data 160 includes data indicating status of project of the user. For example, if the user was preparing an article in a digital publishing application and what was left was publishing the prepared article at the time the user quit the digital publishing application then the application analytics engine 158 tracks the state. Now when the user next opens the digital publishing application on another device then the user is indicated the state and options are provided to the user for publishing using the digital publishing application or any other application. In addition, while preparing the article, a recommendation can also be made by the synchronization engine 132 to incorporate some of other assets saved by the user and relevant for the article. Such a recommendation can be generated using one or more engines, as described herein.

The creative apparatus 108 also includes a community engine 164 which enables creation of various communities and collaboration among the communities. A community, as described herein, includes a group of users that share at least one common interest. The community can be closed, i.e., limited to a number of users or can be open, i.e., anyone can participate. The community enables the users to share each other's work and comment or like each other's work. The work includes the application program data 140. The community engine 164 stores any data corresponding to the community, such as work shared on the community and comments or likes received for the work as community data 166. The community data 166 also includes notification data and is used for notifying other users by the community engine in case of any activity related to the work or new work being shared. The community engine 164 works in conjunction with the synchronization engine 132 to provide collaborative workflows to the user. For example, the user can create an image and can request for some expert opinion or expert editing. An expert user can then either edit the image as per the user liking or can provide expert opinion. The editing and providing of the expert opinion by the expert is enabled using the community engine 164 and the synchronization engine 132. In collaborative workflows, a plurality of users are assigned different tasks related to the work.

The creative apparatus 108 also includes a marketplace engine 168 for providing marketplace to one or more users. The marketplace engine 168 enables the user to offer an asset for selling or using. The marketplace engine 168 has access to the assets 140 that the user wants to offer on the marketplace. The creative apparatus 108 also includes a search engine 170 to enable searching of the assets 140 in the marketplace. The search engine 170 is also a part of one or more application programs 128 to enable the user to perform search for the assets 140 or any other type of the application program data 130. The search engine 170 can perform a search for an asset using the metadata 142 or the file.

The creative apparatus 108 also includes a document engine 172 for providing various document related workflows, including electronic or digital signature workflows, to the user. The document engine 172 can store documents as the assets 140 in the data storage unit 112 or can maintain a separate document repository (not shown in FIG. 1).

Figure 2:
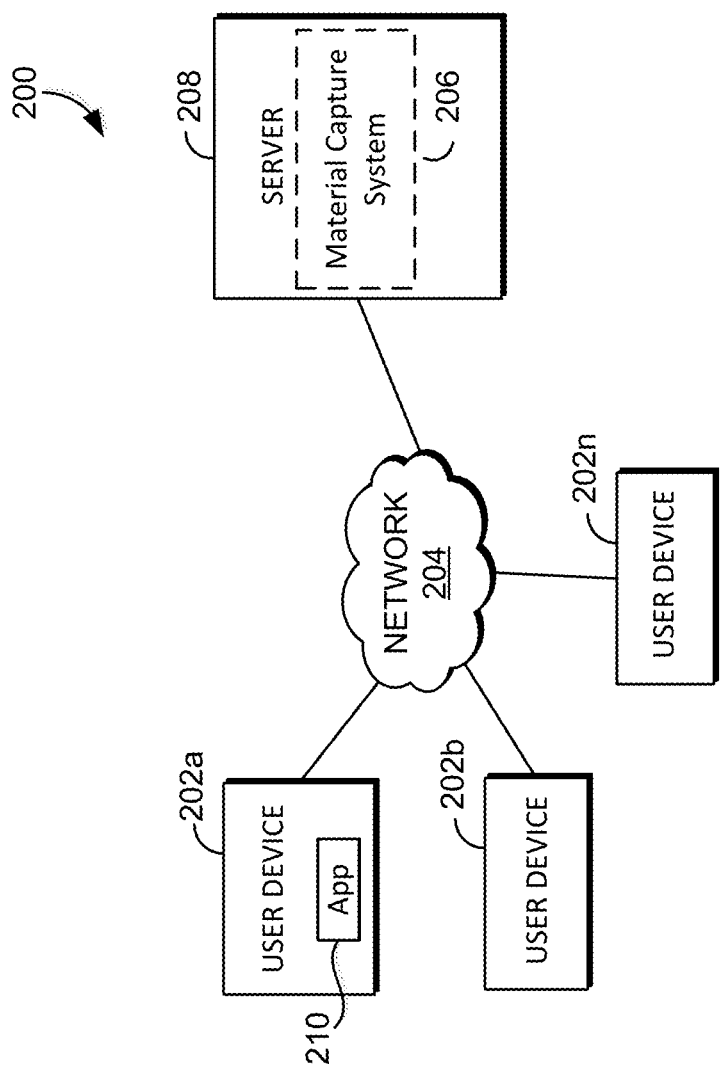
FIG. 2 depicts an example configuration of an operating environment in which some implementations of the present disclosure can be employed, in accordance with various embodiments of the present disclosure.

In accordance with embodiments of the present invention, application programs 128 can include an application, such as application 210 of FIG. 2, which facilitates material capture of an imaged surface. Such an application can be provided to the user device 102A so that the material capture application operates via the user device. In another embodiment, material capture functionality can be provided as an add-on or plug-in to an application, such as a design or image processing application.

FIG. 2 depicts an example configuration of an operating environment in which some implementations of the present disclosure can be employed, in accordance with various embodiments of the present disclosure. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether for the sake of clarity. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, some functions may be carried out by a processor executing instructions stored in memory as further described with reference to FIG. 7.

It should be understood that operating environment 200 shown in FIG. 2 is an example of one suitable operating environment. Among other components not shown, operating environment 200 includes a number of user devices, such as user devices 202a and 202b through 202n, network 204, and server(s) 208. Each of the components shown in FIG. 2 may be implemented via any type of computing device, such as one or more of computing device 700 described in connection to FIG. 7, for example. These components may communicate with each other via network 204, which may be wired, wireless, or both. Network 204 can include multiple networks, or a network of networks, but is shown in simple form so as not to obscure aspects of the present disclosure. By way of example, network 204 can include one or more wide area networks (WANs), one or more local area networks (LANs), one or more public networks such as the Internet, and/or one or more private networks. Where network 204 includes a wireless telecommunications network, components such as a base station, a communications tower, or even access points (as well as other components) may provide wireless connectivity. Networking environments are commonplace in offices, enterprise-wide computer networks, intranets, and the Internet. Accordingly, network 204 is not described in significant detail.

It should be understood that any number of user devices, servers, and other components may be employed within operating environment 200 within the scope of the present disclosure. Each may comprise a single device or multiple devices cooperating in a distributed environment.

User devices 202a through 202n can be any type of computing device capable of being operated by a user. For example, in some implementations, user devices 202a through 202n are the type of computing device described in relation to FIG. 7. By way of example and not limitation, a user device may be embodied as a personal computer (PC), a laptop computer, a mobile device, a smartphone, a tablet computer, a smart watch, a wearable computer, a personal digital assistant (PDA), an MP3 player, a global positioning system (GPS) or device, a video player, a handheld communications device, a gaming device or system, an entertainment system, a vehicle computer system, an embedded system controller, a remote control, an appliance, a consumer electronic device, a workstation, any combination of these delineated devices, or any other suitable device.

The user devices can include one or more processors, and one or more computer-readable media. The computer-readable media may include computer-readable instructions executable by the one or more processors. The instructions may be embodied by one or more applications, such as application 210 shown in FIG. 2. Application 210 is referred to as a single application for simplicity, but its functionality can be embodied by one or more applications in practice. As indicated above, the other user devices can include one or more applications similar to application 210.

The application(s) may generally be any application capable of facilitating the exchange of information between the user devices and the server(s) 208 in carrying out material capture for a material surface. In some implementations, the application(s) comprises a web application, which can run in a web browser, and could be hosted at least partially on the server-side of environment 200. In addition, or instead, the application(s) can comprise a dedicated application, such as an application having image processing functionality. In some cases, the application is integrated into the operating system (e.g., as a service). It is therefore contemplated herein that "application" be interpreted broadly.

In accordance with embodiments herein, the application 210 can facilitate material capture of an imaged material surface. In particular, a user can select or input images and/or a video of the surface of an object. In some embodiments, the surface is generally planar with minor variations. A user may select desired images from a repository, for example, stored in a data store accessible by a network or stored locally at the user device 202a. Alternatively, a user can select or input images and/or a video using, for example, a camera on a device, for example, user device 202a.

Based on the input images and/or video, material capture of a surface can be determined, for instance, at a server, and provided to the user device 202a. In this regard, a material model representing the properties of the surface material can be accessible to a user, for example, within an application, allowing the user to apply the attributes of the surface to the surface of a computer-generated object.

As described herein, server 208 can facilitate material capture via material capture system 206. To perform material capture, server 208 can interact with a user device (e.g., a camera) with imaging functionality. Server 208 includes one or more processors, and one or more computer-readable media. The computer-readable media includes computer-readable instructions executable by the one or more processors. The instructions may optionally implement one or more components of material capture system 206, described in additional detail below.

For cloud-based implementations, the instructions on server 208 may implement one or more components of material capture system 206, and application 210 may be utilized by a user to interface with the functionality implemented on server(s) 208. In some cases, application 210 comprises a web browser. In other cases, server 208 may not be required. For example, the components of material capture system 206 may be implemented completely on a user device, such as user device 202a. In this case, material capture system 206 may be embodied at least partially by the instructions corresponding to application 210.

Thus, it should be appreciated that material capture system 206 may be provided via multiple devices arranged in a distributed environment that collectively provide the functionality described herein. Additionally, other components not shown may also be included within the distributed environment. In addition, or instead, material capture system 206 can be integrated, at least partially, into a user device, such as user device 202a. Furthermore, material capture system 206 may at least partially be embodied as a cloud computing service.

Figure 3:
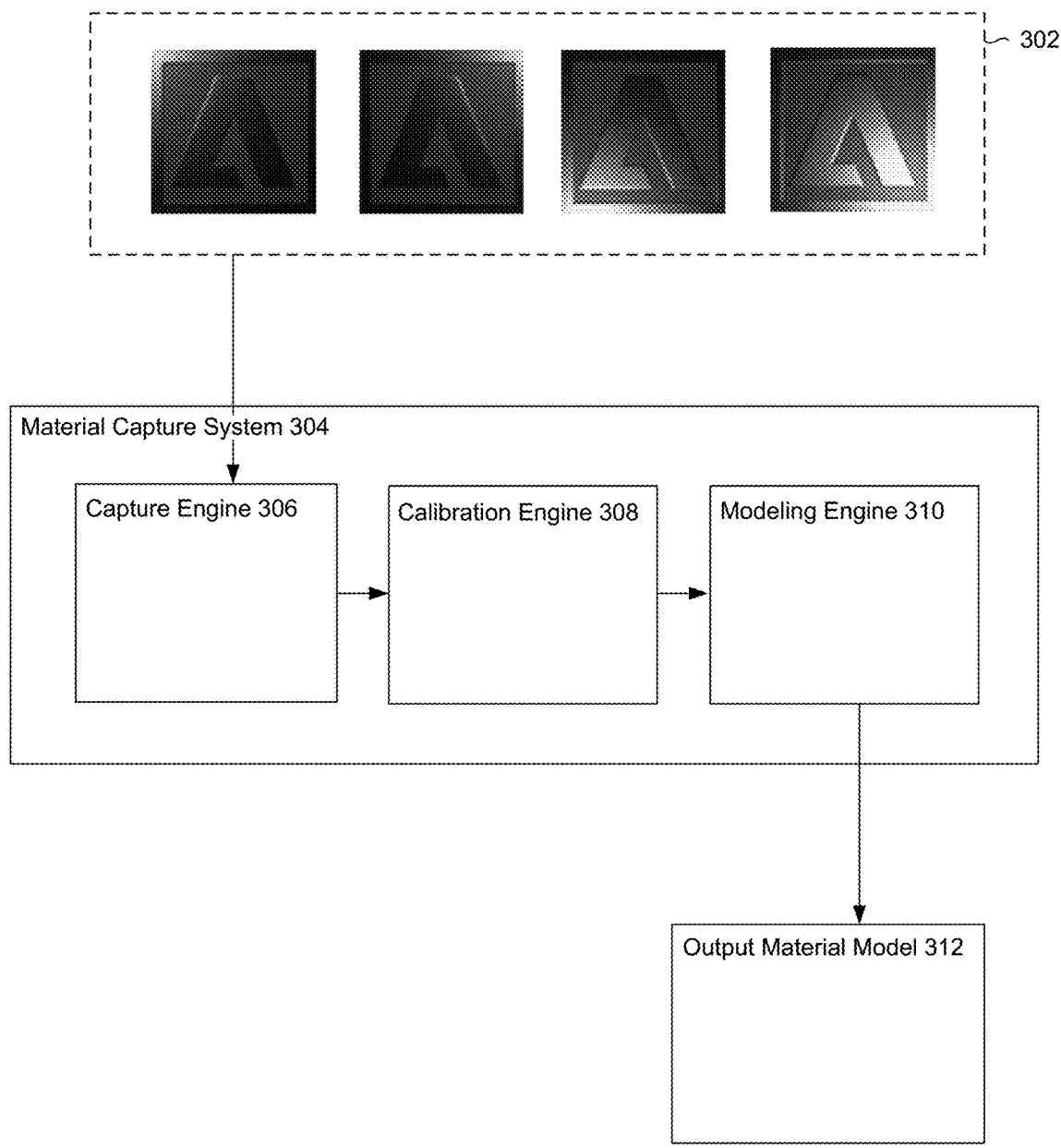
FIG. 3 depicts aspects of an illustrative material capture system, in accordance with various embodiments of the present disclosure.

FIG. 3 depicts an example configuration of an illustrative material capture system 304 for implementing material capture of a surface, in accordance with various embodiments of the present disclosure. Material capture system 304 can be any type of processing system executed by instructions on a computing device. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether for the sake of clarity. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, some functions may be carried out by a processor executing instructions stored in memory as further described with reference to FIG. 7. As depicted in FIG. 3, material capture system 304 includes capture engine 306, calibration engine 308, and modeling engine 310.

Capture engine 306 obtains references or receives images 302 taken of a surface. Such images can be used to produce a material model of the surface captured in the images. Images 302 can be taken using a user device, for example, user device 202a-202n as described with reference to FIG. 2. Such a user device can be a portable user device coupled with an illuminant, for example, a mobile phone with a flash. Images can include two photographs captured at various locations, one image under normal lighting and another image using additional lighting such as, for example, a flash. Alternatively, images 202 can be a short video, or sequence of images, of a surface (e.g., planar surface) using, for example, a mobile phone. In embodiments, images captured using a video can be taken by moving a camera planar to a surface. For example, a camera can be moved in a pattern or grid over a surface, with an illuminated light source, such as a flash. While four images are shown in FIG. 3, it should be appreciated that any number of images and/or any length of video sequence can be received by capture engine 306.

After capture engine 306 obtains references or receives images 302, calibration engine 308 generally performs calibration. In particular, images can be calibrated by first aligning pixels in the received images. Such alignment allows for compiling the different lighting and/or camera positions at one or more corresponding pixels of the same location on the surface. To aid in alignment, a grid can be used as a reference to align the images, for instance, grid points of a checkerboard pattern can be used to determine a rotation and translation matrix for each camera position. Such camera position differences can be used to align the images so that information at one or more pixels can be compiled across the images. Such a checkerboard pattern can be placed on the surface being imaged. In other embodiments, other types of markers can be used to align the images, for example, using a designated reference point.

After aligning pixels, calibration continues by determining the lighting and view direction at pixels using the aligned images. In embodiments, because a light source is rigidly fixed to a camera used to take the images, the position of the light source can be determined from the position of the camera using a pre-determined rotation and translation. Further, a light source can be assumed to be of constant brightness, and the radiometric response of the camera can be assumed to be linear. Radiometric response is a function that transforms sensor irradiance into measured intensities that are the output from the camera.

Because the relative position between the camera and the light source is known, the position of the light source can easily be calculated. As such, the three-dimensional position for pixels in the images can be determined by computing the positions using specified coordinates on, for example, a reference checkerboard. It should be noted that such a determination typically may not provide accurate surface normal estimations. However, using the reference, the different images can be aligned so that all the lighting information at an individual pixel throughout the images can be compiled from the images. Such information from corresponding pixels across information can be used to help determine the lighting and view direction information at points on the imaged surface. This lighting and view information can then be used to determine properties of the surface during material capture to generate a material model.

Once calibration is completed, modeling engine 310 can use the lighting/view information to determine a material model for the material surface. This material model can be based on the BRDF of reference materials, where reference materials are materials exhibiting similar surface properties as the imaged surface. BRDF can be represented as a function $$\rho(\theta_h, \theta_d, \phi_d) \text{ with } \theta_h, \theta_d \in \left[0, \frac{\pi}{2}\right) \text{ and } \phi_d \in [0, \pi).$$

Further, upon incorporating a bivariate representation to express a per-pixel BRDF, an exemplary equation for representing the BRDF is:

$$\hat{\rho}(\theta_h, \theta_d) = \frac{1}{180} \sum_{\phi_d} \hat{\rho}(\theta_h, \theta_d, \phi_d)$$

In such an equation, $\rho$ is used as the bivariate representation of the BRDF. In this way, the material model can represent the BRDF of the imaged surface on a per-pixel basis. When determining material properties of a surface during material capture information about a surface material can be estimated using a database, such as a material library, of reference materials that have had such information previously calculated. Such reference materials can be materials for which the BRDF was previously determined. As such, the BRDF at a pixel can be represented using a set of reference materials selected from a dictionary of reference materials. The process of narrowing the reference material library to the materials that exhibit similar surface properties as the imaged surface is known as global material estimation. The selected reference materials can be represented as $D=[\rho_1, \rho_2, \ldots \rho_M]$, so that the BRDF at a pixel can be expressed as $\rho_p=Dc_p$, $c_p \geq 0$ where $c_p$ represents a coefficient of abundance of a material that is used to determine the properties of a surface material.

Utilizing such reference materials to determine the BRDF at a pixel, instead of solving for high-dimensional vector $\rho_p$, only the abundance, or amount, of coefficient $c_p$ needs to be solved for the pixel, where $c_p$ is proportional to the number of reference materials in the dictionary. For example, if a material surface is represented by a dictionary of two reference materials, the total $c_p$ at a pixel adds up to 100%, for instance, $c_1$ has an abundance of 0.9 (90%) and $c_2$ has an abundance of 0.1 (10%). This means $c_1$ contributes 90% of material properties and $c_2$ contributes 10% of the material properties of the surface undergoing material capture. As such, the BRDF at a pixel can be represented as a weighted combination of the material reference BRDF. The reference materials in the database can be narrowed to a small set of materials that best represent the captured material surface. Such a subset of reference materials from the database, best representing the material captured in the images of the real-world surface, can be used to determine a model that accurately captures the information about the captured material surface. As such, a sparse prior can be incorporated into the BRDF determination to restrict the number of reference materials used and regularize such an under-constrained equation. By assuming that the coefficient of abundance is sparse, the BRDF at a pixel p becomes a linear combination of a select subset of dictionary reference materials that best represent a surface material undergoing material capture.

To fully determine the material model of the properties of the surface undergoing material capture, an example equation for approximating the properties is $$\underset{n_p, c_p}{\operatorname{argmin}} \|I_p - B(n_p, l_p, v_p) \cdot c_p\|_2^2 + \lambda \|c_p\|_1 \qquad \text{(Equation 1)}$$

In such an equation, I denotes image intensities observed at pixel p after calibration of images of the surface. $l_p$ and $v_p$ are the lighting and view directions determined during calibration for the collected images so that $l_p = [l_p^1, l_p^2, \ldots l_p^Q]$, $v_p = [v_p^1, v_p^2, \ldots v_p^Q]$. In this way, the lighting and view direction at a pixel p as determined during calibration is respectively denoted as $l_p^i$ and $v_p^i$ for an image $l_p^k$.

$n_p$ represents the surface normal at pixel p. Surface normal is a vector that is perpendicular to a tangent plane to the surface at a point. B can be a matrix denoted as $B=D(s1^T)$, where s accounts for shading of a lighting direction. As such, s can be represented as $s(i)=\max(0, n_p^T l_p^i)$. As such, for each estimated coefficient c as described above, optimal surface normals can be determined when estimating material properties during material capture.

The three-dimensional positions of the pixels determined during calibration can be used as initial surface normals to solve for abundances using Equation 1 and a library of reference materials. One example of such a library of reference materials is the Mitsubishi Electric Research Laboratories (MERL) BRDF Database. The MERL BRDF Database contains reflectance functions of over 100 different materials, where each reflectance is stored as a densely measured BRDF determined using the traditional, highly time-consuming laboratory setting system. This can output a material response curve of the global materials imitated in the surface, where the peaks in the curve correspond to the reference materials in the material library with similar properties to the captured material surface. Upon creating a material response curve, the top materials with largest response can be selected to reduce the dictionary. The set of materials can then be used to further determine the material properties of the captured surface. This can be done because the BRDF at each pixel can be determined for pixels using a linear combination of a small number of reference materials for which the BRDF and surface normal are already determined.

Using a set of reference materials removes the need to perform complex optimization involving a scarcity constraint, allowing for significant speedups and increased efficiency in the determination of the material model. B can be generated using shading terms associated with the set of reference materials. For example in $$\underset{n_p, c_p}{\operatorname{argmin}} \|I_p - B(n_p, l_p, v_p) \cdot c_p\|_2^2 + \lambda \|c_p\|_1 \text{ the } \lambda \|c_p\|_1$$

can be removed from the equation to become:

$$\underset{n_p, c_p}{\operatorname{argmin}} \|I_p - B(n_p, l_p, v_p) \cdot c_p\|_2^2; c_p > 0. \qquad \text{(Equation 2)}$$

To determine the material properties of the captured surface using reference materials, iterative updates can be performed using, for example, Equation 2, until the error in the output is reduced to below a predetermined threshold. Given the information about the reference materials from the material dictionary, a grid based on elevation and azimuth angles can be constructed where candidate normal can be evaluated to match the per-pixel intensity profile of the imaged material surface. An exemplary equation for expressing such a grid for performing this can be represented as: $\mathcal{N} = \{(\tilde{\theta}, \tilde{\phi}) \| \tilde{\theta} - \hat{\phi} | \leq \mathcal{T}_\theta, | \tilde{\phi} - \hat{\phi}_p | \leq \mathcal{T}_\phi \}$, where $\mathcal{T}_\phi$ and $\mathcal{T}_\phi$ are thresholds to determine cardinality for each candidate set. For each element in $\mathcal{N}$, a candidate surface normal can be computed as $\tilde{n} = [\sin \tilde{\theta} \cos \tilde{\phi}, \sin \tilde{\theta} \sin \tilde{\phi}, \cos \tilde{\theta}]$. As such, an estimate of a surface normal at pixel p can be gives as $$\hat{n}_p = \underset{n_p \in \mathcal{N}}{\operatorname{argmin}} \|I_p - \hat{B}(n_p, l_p, v_p) \cdot c_p\|_2^2.$$

Such an equation can be solved by examining the candidate normal on the grid.

Upon determining a surface normal estimate $\hat{n}_p$, for example, using the above equation, an estimate of abundance, or amount, at a pixel can be determined. An equation that can be used to solve for the abundance is $$\hat{c}_p = \underset{c_p}{\operatorname{argmin}} \|I_p - \hat{B}(n_p, l_p, v_p) \cdot c_p\|_2^2$$

where $c_p \geq 0$. Such an equation can be solved using a non-negative least square. A non-negative least square is a constrained version of the least squares problem where the coefficients are not allowed to become negative. Advantageously, using such a per-pixel estimation framework allows the system to handle complex spatial variations in the BRDF, allowing for variations in a surface to be maintained during material capture.

To determine the abundance of each reference material, iterative updates can be performed using, for example, Equation 1 and/or 2, until the error in the output is reduced to below a predetermined threshold. To perform this determination, a subset of reference materials can be selected for a material library as described above. Given this compact group of reference materials, and the abundances $c_p$ computed based on the set of reference materials, the surface normal can be solved for by searching for estimates of the surface normals that minimize the energy function using, for example, Equation 1 and/or 2. Upon finding new surface normals, Equation 1 and/or 2 can then be used to solve for new abundances. This process can be iteratively performed until the output of Equation 1 and/or 2 falls below a predetermined threshold level. For example, the percentage difference between two iterations falls within a certain percentage of each other, such as 1% or 0.1%.

Once the errors during the iterative updates are reduced below a predetermined threshold, the material model can be output, such as, output material model 312. Upon being output, the material model representing the surface material can be provided to a user, for example, within an application, allowing the user to apply the attributes of the captured surface to the surface of a computer-generated object. Such a material model can be auto applied upon an indication that a particular surface should be applied to the surface of a computer-generated object; for example, a user could image the surface of a checkered couch and indicate that the surface of the couch should be applied to a computer-generated couch. The material capture system as previously described can be used to determine a material model for the material surface of the imaged couch and auto-apply the material model to the computer-generated couch.

Figure 4:
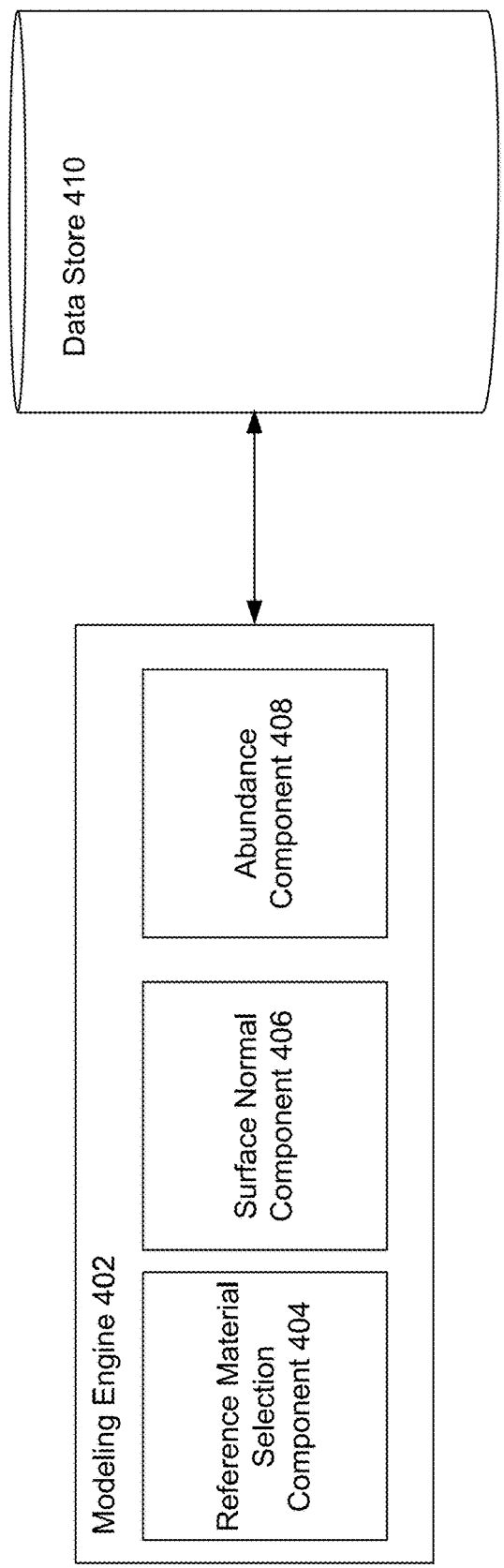
FIG. 4 depicts aspects of an illustrative refining engine, in accordance with various embodiments of the present disclosure.

FIG. 4 depicts an example configuration of an illustrative refining engine for implementing the refining stage of determining the material properties of a surface material during material capture, in accordance with various embodiments of the present disclosure. Modeling engine 402 can be run on any type of processing system executed by instructions on a system run on a computing device, for example material capture system 204 and/or material capture system 304. It should be understood that this and other arrangements described herein are set forth only as examples. Other arrangements and components can be used in addition to or instead of those shown, and some components may be omitted altogether for the sake of clarity. As depicted in FIG. 4, modeling engine 402 is comprised of dictionary reduction component 404, surface normal component 406 and abundance component 408.

Once images taken of a material surface are calibrated, modeling engine 402 can use the calibrated images to determine the properties of the material surface. Refining engine can utilize information from the calibrated images to perform several steps on various components.

Reference material selection component 404 can be utilized to perform global material estimation and determine the set of reference materials to use to determine a material model of the imaged surface. Selecting a set of reference materials analyzed to determine the properties of the surface material greatly reduces the time and computational power required for material capture. To determine the set of reference materials to utilize, three-dimensional positions of the pixels determined during calibration can be used as surface normals to solve for abundances using Equation 1 and a library of reference materials. A library of reference materials can be stored, for example, in data store 410. Using Equation 1 and a library of reference materials can be used to output a material response curve where the peaks in the curve correspond to the materials with similar properties to the captured material surface. Upon creating a material response curve, the top materials with the greatest similarity (e.g., exhibiting the largest response peaks on the material response curve) can be selected to reduce the dictionary.

The selected set of materials can be used because the BRDF at a pixel can be determined using a linear combination of information from the reference materials, such as a predetermined BRDF and surface normal. As such, surface normal component 406 can be used to estimate surface normals for the surface material using information about the reference materials from the material library. For example, if the subset of materials reduces a library from over 100 reference materials down to two reference materials, information about those two reference materials can be used to determine an estimated surface normal that represents the surface material undergoing material capture.

Upon determining surface normals, the BRDF can then be estimated using abundance component 408 to determine abundance levels, or amounts, for the BRDF from the reference materials. For example, if a material surface is represented by a subset of two reference materials from a material library, the total abundance at a pixel will add up to 100%, for instance, if $c_1$ has an abundance of 0.6 (90%) then $c_2$ will have an abundance of 0.4 (10%). As such, the abundance at a pixel can be represented as a weighted combination of the material reference BRDF.

Surface normal component 406 and abundance component 408 can be used to iteratively update the material model until the accuracy is within a predetermined threshold, for instance, indicated by a percentage change between two iterations below a certain amount, for example 0.1%. Such accuracy can be determined using the difference between the energy function determined using, for example, Equation 2 over two or more iterations.

In embodiments, modeling engine 402 can store the optimized model of the surface material properties. The optimized model can be stored in data store 410. Data store 410 can be updated by modeling engine 402 when an optimized material model is determined to be within a threshold percentage of error between iterative updates to determine an optimal representation of the captured material. Having such a data store allows for material models of various materials to be stored. In addition, such a data store can be used to store a library of reference materials used to determine the properties of a surface material during material capture.

Figure 5:
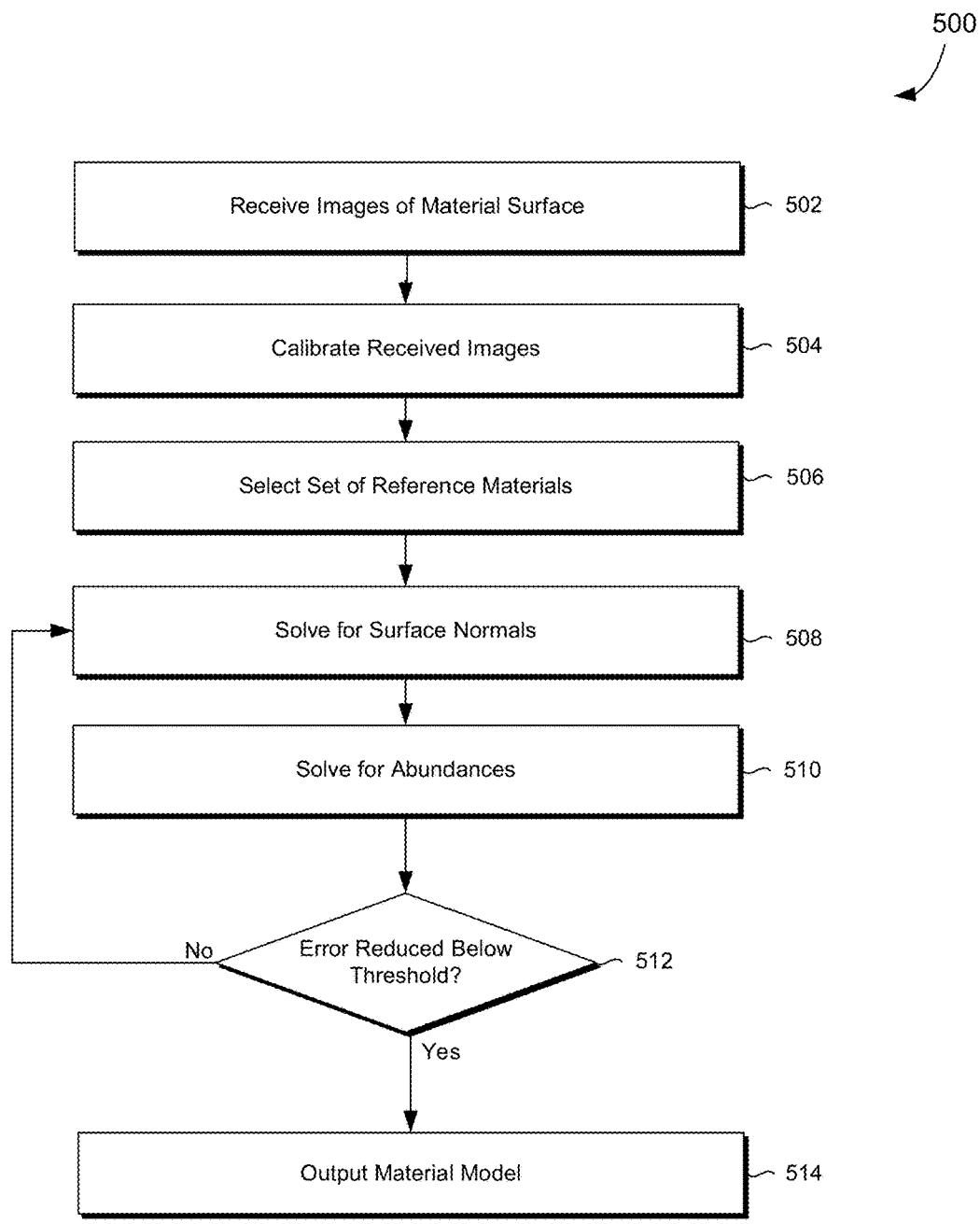
FIG. 5 illustrates a process flow depicting an embodiment performing material capture for a surface material, in accordance with various embodiments of the present disclosure.

FIG. 5 illustrates a process flow 500 depicting an example determination of material properties during material capture of a surface, in accordance with various embodiments of the present disclosure. Process flow 500 can be carried out, for example, by material capture system as discussed with reference to FIG. 3.

As depicted, process flow 500 begins at block 502 where images of the material surface are received. These images can be captured using a commodity device, for instance, a mobile phone. The captured surface should be largely planar, however, small surface variations can be accounted for during the material capture process, for example, where one portion of the surface is 1 cm away from the capture device and another portion of the surface is 1.01 cm away from the capture device. Such images can be captured while a light source on the device is illuminated, providing changing lighting on the surface being calibrated.

At block 504, the received images can be calibrated. The received images can be calibrated by aligning pixels in the images and then determining the different lighting and/or camera positions at corresponding pixels across the images. In particular, the received images can be aligned utilizing, for example, a grid with a point that is constant across all captured images.

At block 506, a set of reference materials can be selected from a dictionary of reference materials, where the set most closely reflect to the properties of the captured material surface. This subset of reference materials can be used to determine the material properties of the captured material surface. To determine such a subset, abundance coefficients can be calculated with sparse priors using three-dimensional information of pixels determined during calibration of the images. These coefficients are then summed across pixels. This can be used to produce a material response curve where the peaks in the curve correspond to the materials with similar properties to the captured material surface. Upon creating the material response curve, the top materials with largest response can be selected to reduce the dictionary. Using such a subset of reference materials removes the need to perform complex optimization involving a scarcity constraint, allowing for significant speedups in the determination of the material model. For example, Equation 1 can be reduced to Equation 2. Such a subset of materials can be used because the BRDF at each pixel can be determined for pixels using a linear combination of a small number of reference materials for which the BRDF and surface normal are already determined.

Once the dictionary of reference materials is reduced to the subset using the response curve, the process then moves to block 508 where surface normals for the material can be solved for using, for example Equations 2. To determine the surface normals, a grid based on elevation and azimuth angles can be specified and searched for candidate normals that best match the profile of the pixels of the captured surface. At block 510, the surface normals determined at block 508 can be used to determine the BRDF of pixels using abundance of the predetermined BRDF of the subset of reference materials.

After determining the abundance, the process can move to block 512 where a determination is made as to whether error of the material model has been reduced below a predetermined threshold. If there is not an error, then the process repeats blocks 508-510 as described above. If there is an error, then the process proceeds to block 514. At bock 514, the material model is output. Such a material model representing the surface material can be provided to a user, for example, within an application, allowing the user to apply the attributes of the captures surface to the surface of a computer-generated object.

Figure 6:
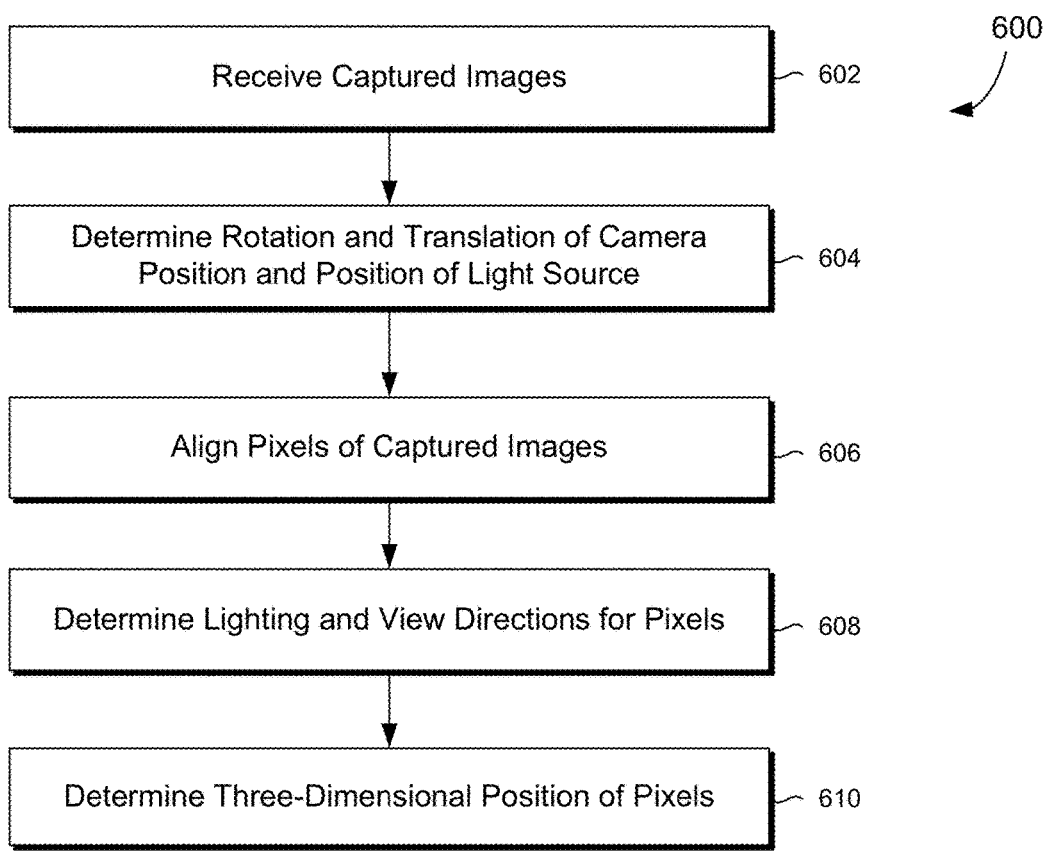
FIG. 6 illustrates a process flow depicting an example calibration of received captured images of a material surface during material capture, in accordance with various embodiments of the present disclosure.

FIG. 6 illustrates a process flow 600 depicting an example calibration of images used for material capture, in accordance with various embodiments of the present disclosure. Such calibration can take place using a calibration engine of a material capture system as described with reference to FIG. 3.

At block 602, captured images are received. Such images can be captured using, for example, a user device such as user device 202a-202n as described with reference to FIG. 2. The captured images can be taken of a largely planar surface with minor variations. Additionally, the images can be taken with an illuminated light source on the capturing device, for example, a mobile phone with an illuminated flash. It should be appreciated that such images can include a set of images and/or a sequence of video.

At block 604, the rotation and translation of the position of the camera used to capture the images received at block 602 can be determined. In addition, at block 604, the position of light source in relation to the camera can be determined. This is possible because the light source and the camera have fixed positions in relation to one another, as such, it is possible to acquire the position of the light source in the captured images. A rotation and translation matrix can also be determined for each camera position.

At block 606, the pixels of the captured images can be aligned. This alignment can be carried out using a grid. A checkerboard can be placed into the frame when a surface material is being imaged so that the captured images contain images of the checkerboard and the material surface. Having a checkerboard that is constant in the images allows for aligning the images using specified portions of the checkerboard to calibrate the images. In this way, a checkerboard allows for determination of the rotation and translation matrix of the camera position.

As such, once the pixels are aligned and the rotation and translation matrix for the camera positions and the position of the light source are determined, at block 608, the lighting and view direction of pixels can be determined. Such information about the lighting and view direction at pixels can be used, for example, in Equations 1 and 2 to determine the properties of the material surface undergoing material capture.

Finally, the three-dimensional position of pixels can be determined at block 610. This information can be used, for example, in Equation 1 to perform global material estimation and reduce Equation 1 to Equation 2 by determining a subset of reference materials that best represent the surface undergoing material capture.

Figure 7:
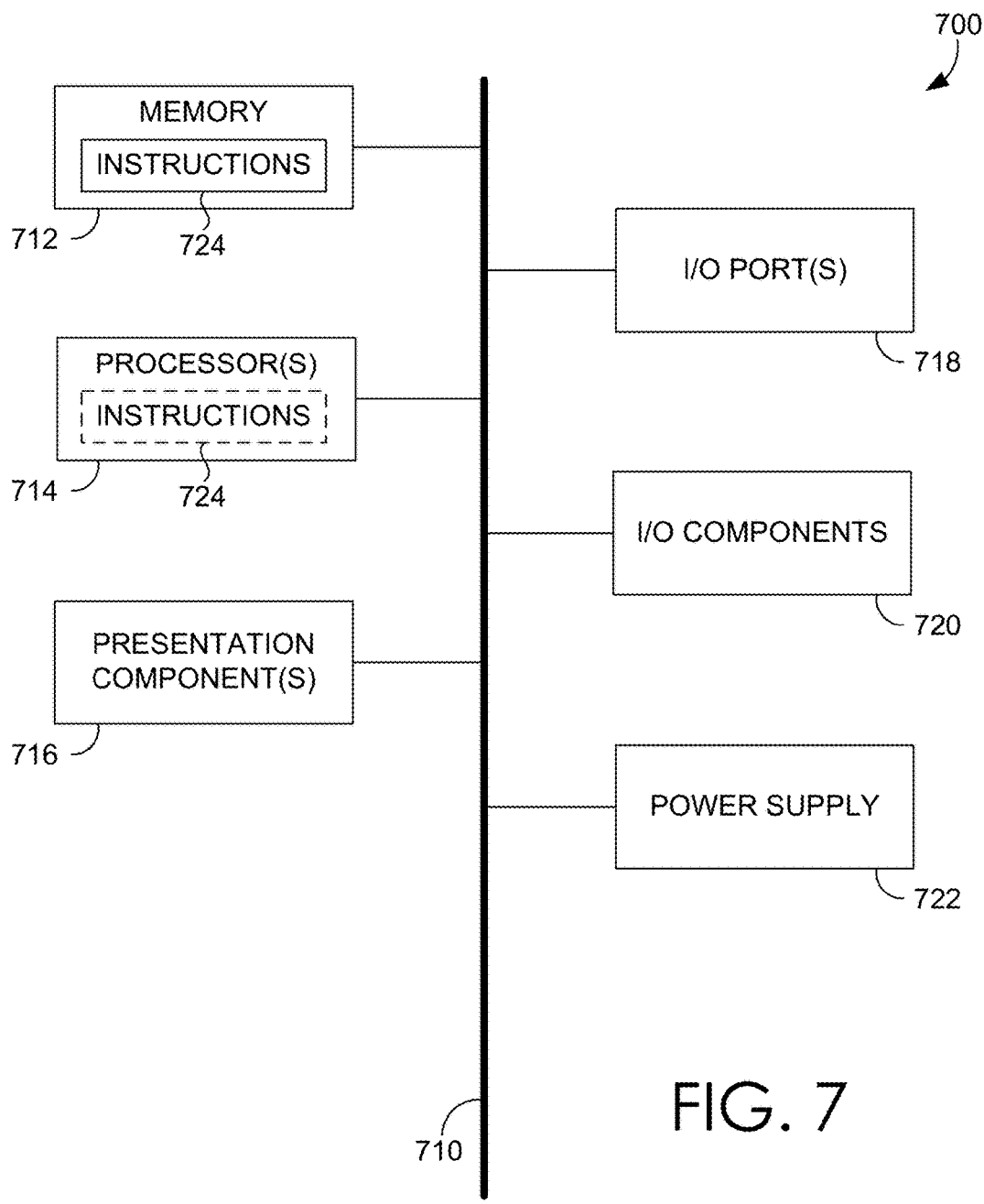
FIG. 7 is a block diagram of an example computing device in which embodiments of the present disclosure may be employed.

Having described embodiments of the present invention, an example operating environment in which embodiments of the present invention may be implemented is described below in order to provide a general context for various aspects of the present invention. Referring to FIG. 7, an illustrative operating environment for implementing embodiments of the present invention is shown and designated generally as computing device 700. Computing device 700 is but one example of a suitable computing environment and is not intended to suggest any limitation as to the scope of use or functionality of the invention. Neither should the computing device 700 be interpreted as having any dependency or requirement relating to any one or combination of components illustrated.

Embodiments of the invention may be described in the general context of computer code or machine-useable instructions, including computer-executable instructions such as program modules, being executed by a computer or other machine, such as a smartphone or other handheld device. Generally, program modules, or engines, including routines, programs, objects, components, data structures, etc., refer to code that perform particular tasks or implement particular abstract data types. Embodiments of the invention may be practiced in a variety of system configurations, including hand-held devices, consumer electronics, general-purpose computers, more specialized computing devices, etc. Embodiments of the invention may also be practiced in distributed computing environments where tasks are performed by remote-processing devices that are linked through a communications network.

With reference to FIG. 7, computing device 700 includes a bus 710 that directly or indirectly couples the following devices: memory 712, one or more processors 714, one or more presentation components 716, input/output ports 718, input/output components 720, and an illustrative power supply 722. Bus 710 represents what may be one or more busses (such as an address bus, data bus, or combination thereof). Although the various blocks of FIG. 7 are shown with clearly delineated lines for the sake of clarity, in reality, such delineations are not so clear and these lines may overlap. For example, one may consider a presentation component such as a display device to be an I/O component, as well. Also, processors generally have memory in the form of cache. We recognize that such is the nature of the art, and reiterate that the diagram of FIG. 7 is merely illustrative of an example computing device that can be used in connection with one or more embodiments of the present disclosure. Distinction is not made between such categories as "workstation," "server," "laptop," "hand-held device," etc., as all are contemplated within the scope of FIG. 7 and reference to "computing device."

Computing device 700 typically includes a variety of computer-readable media. Computer-readable media can be any available media that can be accessed by computing device 700 and includes both volatile and nonvolatile media, removable and non-removable media. By way of example, and not limitation, computer-readable media may comprise computer storage media and communication media.

Computer storage media include volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 700. Computer storage media excludes signals per se.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 712 includes computer storage media in the form of volatile and/or nonvolatile memory. As depicted, memory 712 includes instructions 724. Instructions 724, when executed by processor(s) 714 are configured to cause the computing device to perform any of the operations described herein, in reference to the above discussed figures, or to implement any program modules described herein. The memory may be removable, non-removable, or a combination thereof. Illustrative hardware devices include solid-state memory, hard drives, optical-disc drives, etc. Computing device 700 includes one or more processors that read data from various entities such as memory 712 or I/O components 720. Presentation component(s) 716 present data indications to a user or other device. Illustrative presentation components include a display device, speaker, printing component, vibrating component, etc.

I/O ports 718 allow computing device 700 to be logically coupled to other devices including I/O components 720, some of which may be built in. Illustrative components include a microphone, joystick, game pad, satellite dish, scanner, printer, wireless device, etc.

Embodiments presented herein have been described in relation to particular embodiments which are intended in all respects to be illustrative rather than restrictive. Alternative embodiments will become apparent to those of ordinary skill in the art to which the present disclosure pertains without departing from its scope.

From the foregoing, it will be seen that this disclosure in one well adapted to attain all the ends and objects hereinabove set forth together with other advantages which are obvious and which are inherent to the structure.

It will be understood that certain features and sub-combinations are of utility and may be employed without reference to other features or sub-combinations. This is contemplated by and is within the scope of the claims.

In the preceding detailed description, reference is made to the accompanying drawings which form a part hereof wherein like numerals designate like parts throughout, and in which is shown, by way of illustration, embodiments that may be practiced. It is to be understood that other embodiments may be utilized and structural or logical changes may be made without departing from the scope of the present disclosure. Therefore, the preceding detailed description is not to be taken in a limiting sense, and the scope of embodiments is defined by the appended claims and their equivalents.

Various aspects of the illustrative embodiments have been described using terms commonly employed by those skilled in the art to convey the substance of their work to others skilled in the art. However, it will be apparent to those skilled in the art that alternate embodiments may be practiced with only some of the described aspects. For purposes of explanation, specific numbers, materials, and configurations are set forth in order to provide a thorough understanding of the illustrative embodiments. However, it will be apparent to one skilled in the art that alternate embodiments may be practiced without the specific details. In other instances, well-known features have been omitted or simplified in order not to obscure the illustrative embodiments.

Various operations have been described as multiple discrete operations, in turn, in a manner that is most helpful in understanding the illustrative embodiments; however, the order of description should not be construed as to imply that these operations are necessarily order dependent. In particular, these operations need not be performed in the order of presentation. Further, descriptions of operations as separate operations should not be construed as requiring that the operations be necessarily performed independently and/or by separate entities. Descriptions of entities and/or modules as separate modules should likewise not be construed as requiring that the modules be separate and/or perform separate operations. In various embodiments, illustrated and/or described operations, entities, data, and/or modules may be merged, broken into further sub-parts, and/or omitted.

The phrase "in one embodiment" or "in an embodiment" is used repeatedly. The phrase generally does not refer to the same embodiment; however, it may. The terms "comprising," "having," and "including"" are synonymous, unless the context dictates otherwise. The phrase "A/B" means "A or B." The phrase "A and/or B" means "(A), (B), or (A and B)." The phrase "at least one of A, B and C" means "(A), (B), (C), (A and B), (A and C), (B and C) or (A, B and C)."

What is claimed is:

1. A computer-implemented method for material capture of a surface, comprising:
   receiving a plurality of images, each of the plurality of images depicting a material surface;
   aligning the plurality of images based on alignment of corresponding pixels associated with each of the plurality of images;
   determining reflectance information for at least a portion of the corresponding pixels associated with each of the plurality of images;
   selecting a set of reference materials that represent properties of the material surface based on the determined reflectance information, the selected reference materials representing properties of the material surface;
   generating a material model using the set of reference materials in conjunction with the determined reflectance information; and
   outputting the material model of the material surface.

2. The computer-implemented method for material capture of a surface of claim 1, wherein determining the reflectance information includes finding lighting and view directions for at least one pixel of the corresponding pixels.

3. The computer-implemented method for material capture of a surface of claim 2, wherein a reference grid is used for aligning the plurality of images.

4. The computer-implemented method for material capture of a surface of claim 1, further comprising:

determining a surface normal estimate at a selected pixel;
determining a material coefficient abundance estimate at the selected pixel;
iteratively updating the surface normal estimate and updating the material coefficient abundance estimate at the selected pixel until error is reduced below a predetermined threshold.

5. The computer-implemented method for material capture of a surface of claim 4, wherein the surface normal estimate is determined utilizing a local neighborhood search of a grid based on elevation and azimuth angles for the set of reference materials.

6. The computer-implemented method for material capture of a surface of claim 4, wherein the material coefficient abundance estimate is determined utilizing a non-negative least squares approach based on inputting the surface normal estimate.

7. The computer-implemented method for material capture of a surface of claim 1, further comprising:
determining a surface normal estimate at a selected pixel;
determining a material coefficient abundance estimate at the selected pixel;
updating the surface normal estimate and updating the material coefficient abundance estimate at the selected pixel in parallel until error is reduced below a predetermined threshold.

8. The computer-implemented method for material capture of a surface of claim 1, wherein selecting the set of reference materials includes generating a sparse response curve for a library of reference materials, wherein reference materials with a response on the sparse response curve are selected as the set of reference materials.

9. The computer-implemented method for material capture of a surface of claim 1, wherein a user can apply the material model of the material surface to a surface of a computer-generated object during rendering of the computer-generated object.

10. One or more non-transitory computer-readable storage media having instructions stored thereon, which, when executed by one or more processors of a computing device, cause the computing device to:
receive a plurality of images, the plurality of images depicting a material surface;
calibrate the plurality of images, wherein calibration utilizes a grid depicted in the plurality of images to align the plurality of images and determine reflectance information for at least a portion of the aligned plurality of images;
select a set of reference materials using the calibrated plurality of images;
determine material properties for the material surface at a selected pixel using the set of reference materials; and
output a material model of the material surface based on the determined material properties.

11. The one or more non-transitory computer-readable storage media of claim 10, wherein the reflectance information includes lighting and view directions for at least one pixel of the plurality of images.

12. The one or more non-transitory computer-readable storage media of claim 10, wherein instructions further cause the computing device to:
determine a surface normal estimate at the selected pixel;
determine a material coefficient abundance estimate at the selected pixel;
iteratively update the surface normal estimate and update the material coefficient abundance estimate at the selected pixel until error is reduced below a predetermined threshold.

13. The one or more non-transitory computer-readable storage media of claim 12, wherein the surface normal estimate is determined utilizing a local neighborhood search of a grid based on elevation and azimuth angles for the set of reference materials.

14. The one or more non-transitory computer-readable storage media of claim 12, wherein the material coefficient abundance estimate is determined utilizing a non-negative least squares approach based on inputting the surface normal estimate.

15. The one or more non-transitory computer-readable storage media of claim 10, wherein instructions further cause the computing device to:
determine a surface normal estimate at the selected pixel;
determine a material coefficient abundance estimate at the selected pixel;
update the surface normal estimate and update the material coefficient abundance estimate at the selected pixel in parallel until error is reduced below a predetermined threshold.

16. The one or more non-transitory computer-readable storage media of claim 10, wherein determining global material estimation includes generating a sparse response curve for a library of reference materials, wherein reference materials with a response on the sparse response curve are selected as the set of reference materials.

17. A computing system comprising:
one or more processors; and
one or more non-transitory computer-readable storage media, coupled with the one or more processors, having instructions stored thereon, which, when executed by the one or more processors, cause the computing system to provide:
means for capturing a plurality of images depicting a material surface;
means for calibrating the plurality of images;
means for selecting a set of reference materials;
means for determining material properties for the material surface at a selected pixel using the set of reference materials;
means for outputting a material model of the material surface based on the determined material properties for the material surface; and
means for applying the material model of the material surface to a surface of a computer-generated object.

18. The computing system of claim 17 further comprising:
means for determining a surface normal estimate at the selected pixel;
means for determining a material coefficient abundance estimate at the selected pixel;
means for updating the surface normal estimate and updating the material coefficient abundance estimate at the selected pixel until error is reduced below a predetermined threshold.

19. The computing system of claim 17, wherein determining global material estimation includes generating a sparse response curve for a library of reference materials, wherein reference materials with a response on the sparse response curve are selected as the set of reference materials.

20. The computing system of claim 17, wherein the material coefficient abundance estimate is determined utilizing a non-negative least squares approach based on inputting the surface normal estimate.

* * * * *